(12) United States Patent
Malmqvist

(10) Patent No.: US 8,394,646 B2
(45) Date of Patent: Mar. 12, 2013

(54) METHOD FOR THE QUALITY CONTROL OF MOLECULES OR TARGETS

(75) Inventor: Magnus Malmqvist, Uppsala (SE)

(73) Assignee: Ridgeview Instruments AB, Uppsala (SE)

( * ) Notice: Subject to any disclaimer, the term of this patent is extended or adjusted under 35 U.S.C. 154(b) by 838 days.

(21) Appl. No.: 12/456,792

(22) Filed: Jun. 23, 2009

(65) Prior Publication Data

US 2009/0263917 A1    Oct. 22, 2009

Related U.S. Application Data

(63) Continuation of application No. PCT/SE2008/050054, filed on Jan. 17, 2008.

(51) Int. Cl.
*G01N 33/543* (2006.01)
(52) U.S. Cl. ......... 436/518; 435/6.1; 435/7.1; 435/7.92; 436/501; 436/504
(58) Field of Classification Search .................. None
See application file for complete search history.

(56) References Cited

U.S. PATENT DOCUMENTS

| | | | |
|---|---|---|---|
| 5,110,911 A | 5/1992 | Samuel et al. | |
| 2003/0198638 A1* | 10/2003 | Watkins | 424/143.1 |
| 2005/0019836 A1 | 1/2005 | Vogel et al. | |

FOREIGN PATENT DOCUMENTS

| | | |
|---|---|---|
| WO | WO 2005/080967 A1 | 9/2005 |
| WO | WO 2006/135309 A2 | 12/2006 |

OTHER PUBLICATIONS

Search Report mailed Apr. 17, 2008 issued by the International Searching Authority in counterpart International Application No. PCT/SE2008/050054 (6 pages), Apr. 17, 2008.

Written Opinion mailed Apr. 4, 2008 of the International Searching Authority issued in counterpart International Application No. PCT/SE2008/050054 (11 pages), Apr. 4, 2008.

Susan L. Hefle and Debra M. Lambrecht, "Validated Sandwich Enzyme-Linked Immunosorbent Assay for Casein and Its Application to Retail and Milk-Allergic Complaint Foods," *Journal of Food Protection*, vol. 67, Issue 9, Sep. 2004, Abstract (2 Pages).

Nobuo Sugo, Kyousuke Yokota, Kousuke Kondo, Naoyuki Harada, Yoshinori Aoki, Chikao Miyazaki, Masaaki Nemoto, Toshiyuki Kano, Hitoshi Ohishi and Yoshikatsu Seiki, "Early Dynamic $^{201}$TI SPECT in the evaluation of brain tumours," *Nuclear Medicine Communications*, 2006, 27: pp. 143-149 (7 pages).

Dirk Pauleit, MD, Andre Zimmermann, MD, Gabriele Stoffels, MD, Dagmar Bauer, PhD, Jörn Risse, MD, Michael O. Flüss, MD, Kurt Hamacher, PhD, Heinze H. Coenen, PhD, and Karl-Josef Langen, MD, "$^{18}$F-FET PET Compared with $^{18}$F-FDG PET and CT in Patients with Head and Neck Cancer," *The Journal of Nuclear Medicine*, vol. 47, No. 2, Feb. 2006 (6 pages).

Robert M. Sharkey, Ph.D. and David M. Goldenberg, Sc.D, M.D., "Advances in Radioimmunotherapy in the Age of Molecular Engineering and Pretargeting," *Cancer Investigation*, No. 24: 2006, pp. 82-97 (16 Pages).

\* cited by examiner

*Primary Examiner* — Gary W Counts
(74) *Attorney, Agent, or Firm* — Robert P. Michal; Lucas & Mercanti, LLP

(57) ABSTRACT

A method for quality control of species used in analytical or diagnostic or therapeutic procedures includes immobilization of a model of the malignancy to a solid support (121), contacting the solid support with species dissolved in liquid (122), measuring both the rate of formation of complex and absolute magnitude of number of complexes of model and species (123) and determining the quality of species by comparing the measured values with predetermined values.

10 Claims, 3 Drawing Sheets

Fig. 4(a)
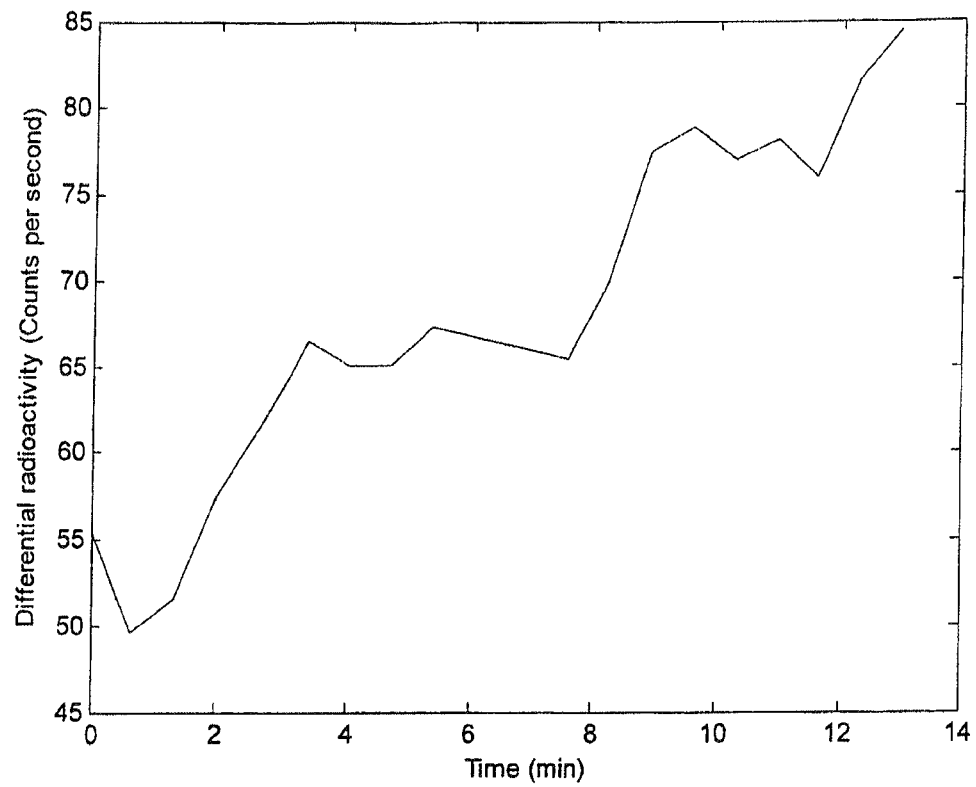
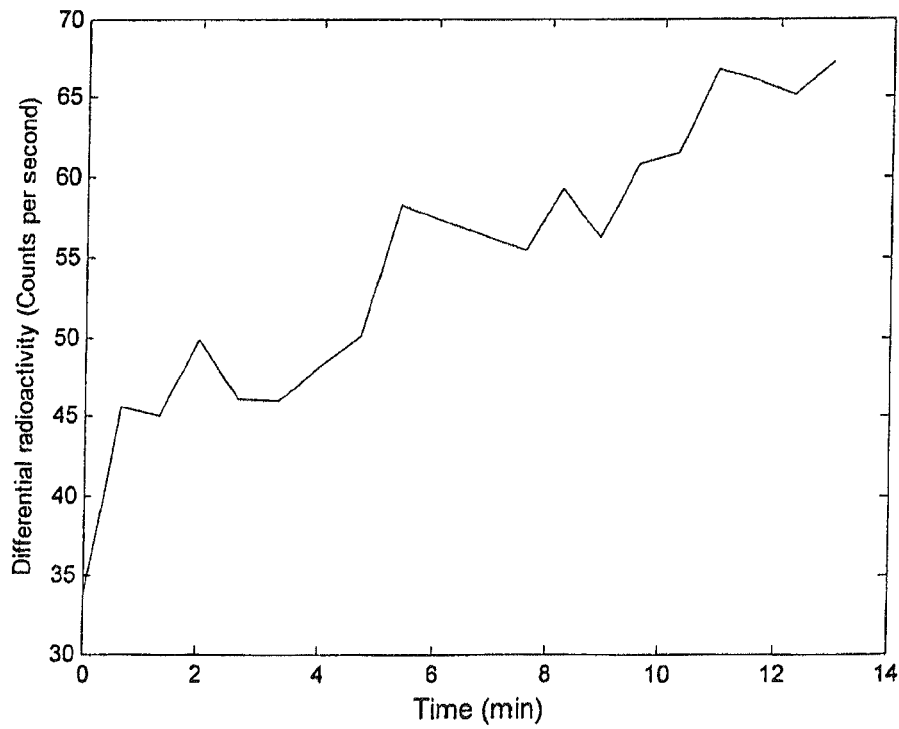
Fig. 4(b)

METHOD FOR THE QUALITY CONTROL OF MOLECULES OR TARGETS

CROSS-REFERENCE TO RELATED APPLICATIONS

This is a continuation of International Application PCT/SE2008/050054 filed Jan. 17, 2008, which claims priority under 35 USC 119 of Swedish Patent Application No. SE 0700101-09 filed Jan. 18, 2007, the entire disclosure of each of which is incorporated herein by reference.

FIELD OF INVENTION

The present invention relates to the field of quality control of different species used for analytical or diagnostic or therapeutic purposes. More in particular, it relates to a method where the different species bind—specifically to objects of some kind. Even more in particular, it relates to quality control of species of biological or chemical origin, e.g. proteins, DNA, RNA, tissue, synthesized chemical compounds and the like, wherein said species is being part of an analytic or diagnostic method or procedure.

BACKGROUND OF THE INVENTION

Analytical or diagnostic or therapeutic procedures are crucial in many functions in the modern society. One of the most common is the diagnostic procedures performed at health care institutions (e.g. hospitals) with the purpose to determine if a patient has a selected disease. For example, elevated concentration of the prostate specific antigen (PSA) in male blood is an indication of ongoing prostate cancer in the patient. Other analytical or diagnostic or therapeutic procedures include, but are not limited to, the diagnosis of cattle prior to slaughter in order to produce safe food, diagnostic procedures in veterinary sciences with the purpose of treating sick animals, targeted radiotherapy of tumors in animal or humans, the detection of pathogens or toxins in food or feed stuff, the determination of the concentration of nutritional supplements (e.g. vitamins) in processed food or feed stuff, the detection of hazardous chemicals in the environment and the like.

One particular method for diagnosis is positron emission tomography (PET). PET can depict the location of the radioactive decay of positron emitting nuclides. Diagnostic PET procedures are developed for a multitude of diseases, most notably for cancers (as evident in the report "18F-FET PET Compared with 18F-FDG PET and CT in Patients with Head and Neck Cancer." by Pauleit D, Zimmermann A, Stoffels G, Bauer D, Risse J, Fluss M O, Hamacher K, Coenen H H, Langen K J. published in Journal of Nuclear Medicine. 2006 February; 47(2):256-261, which is incorporated by reference herein). In all cases, the object under investigation must be contacted with a bi-functional species. Firstly, the species should interact with features of or be part of the function to be diagnosed. Secondly, the species should carry positron emitting nuclides. In case the object is a human and the purpose is to diagnose a possible cancer disease, the species could be an antibody specifically recognizing tumor cells, where the antibody has been labeled with fluorine-18 (a nuclide known to emit positrons), carbon-11 or another nuclide emitting positrons.

Another method for diagnosis is single photon emission computed tomography (SPECT). SPECT can depict the location of the radioactive decay of certain gamma emitting nuclides, such as technetium-99 or iodine-123, in a similar fashion to PET, as evident in the report "Early dynamic 201Tl SPECT in the evaluation of brain tumours." by Sugo N, Yokota K, Kondo K, Harada N, Aoki Y, Miyazaki C, Nemoto M, Kano T, Ohishi H, Seiki Y. published in Nuclear medicine communications. 2006 February; 27(2): 143-9, which is incorporated by reference herein.

One example of therapy is the so-called targeted radiotherapy (described in the report "Advances in radioimmunotherapy in the age of molecular engineering and pretargeting." by Sharkey R M, Goldenberg D M. published in Cancer Investigation. 2006; 24(1):82-97, which is incorporated by reference herein), used mainly in treatment of selected cancers. In such therapy, aggressively radiating nuclides are immobilized to molecules that selectively bind to cancer cells. Upon injection of the radiating molecules in the blood stream of an animal or a human, the molecules will accumulate on cancer cells and be present in low concentration elsewhere in the body. Thus, the radiation source is brought very close to the cancerous tissue, thereby maximizing the radioactive dose to the cancer cells and sparing the remaining body from radiation.

The treatment can also be performed with molecules directing the immune defense to the therapeutic target or by conjugates of target specific molecules and other functions causing damage to specific cells.

One major problem with analytic and diagnostic and therapeutic procedures in general and PET in particular is that the quality of the result is very much dependent on the quality of the species used in the procedure. In some cases, the species are fragile molecules that may alter in function and reliability in transit from manufacturer to end user. Species suitable for PET is one example, where it is known that some of the commonly used positron emitting nuclides have half lives of hours (fluorine-18 has a half life of 110 minutes). Species suitable for targeted radiotherapy is a second example, where the emitting nuclides also have short half lives, such as iodine 131 with a half life of 8 days. It is therefore not certain that the quality control of the species performed at the site of manufacturing is valid when the species arrives at the end user site.

This invention describes a simple and rapid method for quality control of species or targets or intermediates at different steps in the production of species or targets at the end user site which would increase the reliability of commonly performed analytical and diagnostic procedures.

CLOSEST PRIOR ART

Species used for analytical or diagnostic or therapeutic procedures are currently tested for proper quality at the site of manufacturing, and the end user relies on the quality of the species being maintained after transportation. This assumption is in many cases reasonable, in particular when the species are stable molecules with a proven storage life vastly exceeding the time of transport In many cases the production takes place in close vicinity of the user due to short half life or other stability reasons. In rare cases, the species undergo a second quality control at the end user site. Methods used for quality control of species of biological origin, irrespective if performed at the manufacturer's site or at the end user site, include (but are not limited to) spectrophotometry (to determine concentration by use of the extinction coefficient of the species); immunofluorescense, enzyme-linked immunosorbent assay, or similar (to test if the species interacts properly with structures on an test object known to give a positive result in the test) and; bacteriological tests (to prove that the species is sterile). One suitable method for quality control of species is described in the report "Validated sandwich enzyme-linked immunosorbent assay for casein and its application to retail and milk-allergic complaint foods" by Hefle S L, and Lambrecht D M, published in Journal of Food Proteins, 67(9):1933-8, 2004, which is incorporated by reference herein.

SUMMARY OF THE INVENTION

One object of the present invention is to facilitate the quality control of species used for analytical or diagnostic or therapeutic purposes. The invention is particularly useful for quality control near or at the end user site. Another object is to enable analysis or diagnosis based on detection of interactions of targets derived from a malignancy and a known species capable of interacting with said target(s).

In one aspect the invention provides a method for quality control of species used in analytical or diagnostic or therapeutic procedures.

The method comprises providing a solid support having a model system immobilized thereon and a solution wherein the species is dissolved, and detection both of the presence of interaction between species and model and of the rate of formation of complexes of species and model, wherein the criteria for accepting or rejecting species for use in an analytic or diagnostic or therapeutic procedure are at least in part based on the obtained readings of both presence of interaction between species and model and rate of formation of species-model complexes.

In a preferred embodiment the invention provides a method for the verification of interaction between the analytical or diagnostic or therapeutic species of biological origin and a target (said target being a model of the condition being analyzed, diagnosed or treated) by use of time resolved detection of species immobilized to a solid support. When immobilizing the model on a selected portion of a solid support and exposing said model to a solution containing species, a measurement, capable of detecting an interaction between said model and said species can be performed when the amount of solution covering the selected portion of the support is reduced prior to performing said measurement and a reference measurement is performed on a portion of said support where no interaction takes place.

In a further aspect, the invention provides a method for the analytical or diagnostic procedure comprising use of one known species of biological origin (said species being dissolved in liquid) and an unknown target (said target being the analyzed or diagnosed object). The analytical or diagnostic procedure further relies on detection of both presence of interaction between species and target and target and rate of formation of complexes of species and target, wherein the species is detected using a non-contact detection (e.g. a radio-activity detector or as fluorescence detector) and wherein the determination of the properties of said target are at least in part based on the obtained readings of both presence of interaction between species and target and rate of formation of species-target complexes.

In yet a further aspect, the present invention also relates to a kit of targets or ligands or solid supports usable for quality control by the method according to the invention.

BRIEF DESCRIPTION OF THE DRAWINGS

The present invention will be disclosed in closer detail in the description and example below, with reference to the accompanying drawing, in which

FIGS. 4A and 4B show two examples of data from an antibody binding to cancer cells acquired in real time during 13 minutes.

DETAILED DESCRIPTION OF THE INVENTION

Figure 1:
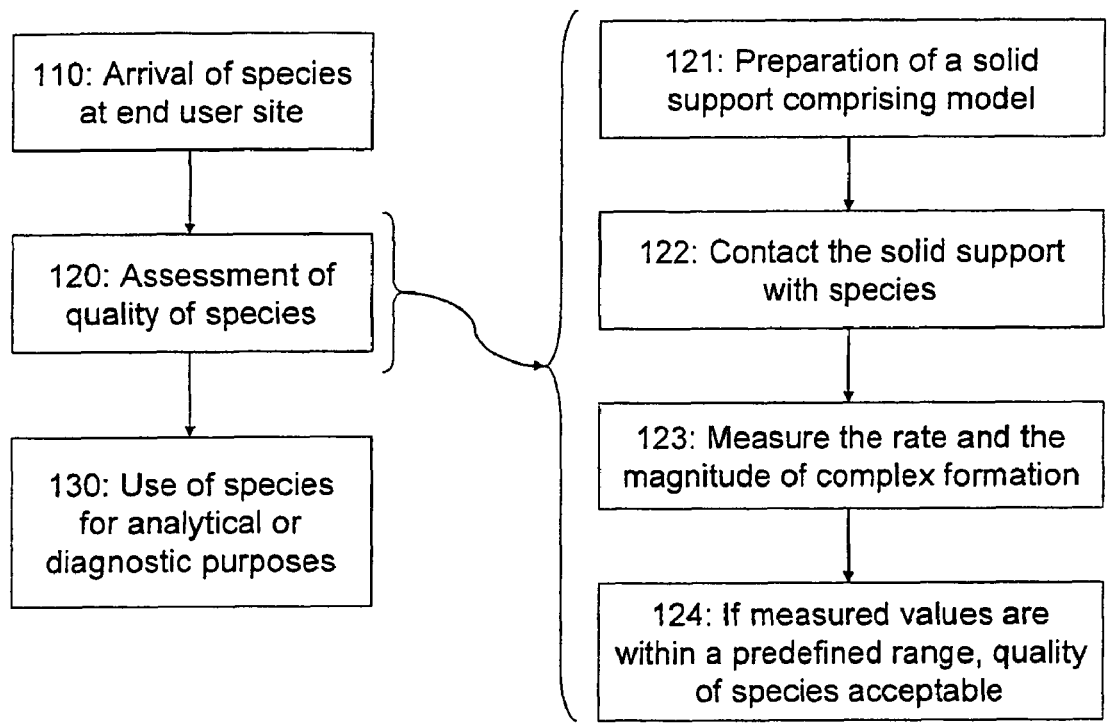
FIG. 1 shows flow scheme for the quality control of species.

For the purpose of the present application, and for clarity, a model of malignancy immobilized to a solid support may be denoted "target" and a species present in a liquid may be denoted "ligand". Possible models include, but are not limited to, tissue samples, embedded tissue samples and sections thereof, cells, bacteria, viruses, solid particles, magnetic particles, macromolecules (e.g. proteins, DNA, RNA) and other chemical compounds, chemically modified surfaces, surface coatings (e.g. paint) or any combination thereof. Possible species for use in analytical or diagnostic or therapeutic procedures include macromolecules (e.g. proteins, DNA, RNA), other chemical compounds and any species that can be dissolved in a liquid or even cells, organelles or organisms that can be suspended in a liquid. The species are either inherently fluorescent or radioactive, or have some sort of label attached. Suitable labels include, but are not limited to, radioactive labels and fluorescent labels. The term "manufacturer" refers to any party making or in other ways supplying species for analytical or diagnostic or therapeutic procedures. The term "end user site" refers to the locale where the actual procedure is performed, e.g. a hospital, a clinical chemistry laboratory, general heath care providers and the like. It is possible that the site of manufacturing and the end user site are in close proximity or are the same.

The present invention also includes kits of targets or ligands or solid supports used for quality control by the method.

Generally, the invention in its first aspect is based on the provision of three characteristic components.

A species suitable for an analytical or diagnostic measurement, labeled with a detectable tracer, A model of the malignancy to be detected, A time resolved measurement of the interaction between the species and the model.

The species suitable for an analytical or diagnostic measurement is normally the reagent supplied from a commercial vendor for use in a particular analytical or diagnostic or therapeutic procedure. The model of the malignancy is typically a cell-line expressing the unique features of the malignancy (e.g. a human cancer cell-line in case the species is used for cancer detection). Possible models also include (but are not limited to) proteins attached to a part of a solid support, multi-cellular organisms (living or dead) attached to a part of a solid support, paint or other surface coatings covering a part of a solid support, one or more pieces of tissue attached to a part of a solid support, or particles attached to a part of a solid support. A suitable apparatus for performing the time resolved measurement is the device described in WO2005080967, which is incorporated by reference herein.

The present invention aims i.a. at improving the quality control of species for use in analytical or diagnostic or therapeutic procedures by enabling a rapid and affordable quality test at the end user site, in which the end user can verify that the species to be used for analytical or diagnostic or therapeutic purposes have desirable quality. In some procedures, the required species are known to be fragile and may therefore degrade in quality in transit from the manufacturer's site to the end user site. For example, diagnostic PET requires that a spontaneously and rapidly degrading species is injected into the patient's blood-stream. For reasons of patient safety and diagnostic accuracy, it is of outermost importance that the species have desired quality at time of use.

The present invention also aims at improving the quality control of species or intermediates in the production of species for use in analytical or diagnostic procedures at the manufacturer's site.

The method used for quality control is outlined in FIG. 1. When a species arrives at the end user site (110), an assessment of the quality of the species is performed (120) followed by use of the species for analytical or diagnostic or therapeutic purposes (130) under the condition that the quality of the species was acceptable. The process of determining the quality of the species is further defined as follows. In a first step (121), a solid support housing the model is prepared. This may be done well in advance. Then (122), the species is brought into contact with the solid support. After that (123), the rate of formation of complexes between the species and the model is measured, as well as the magnitude of the number of formed complexes. In a fourth step (124), the measured entities are compared to predefined values stating the acceptable rate of formation and magnitude of the number of formed complexes.

There are several methods available for the measurement of the rate of complex formation and the magnitude of formed complexes between a species and the model. As examples spectrophotometry (to determine concentration by use of the extinction coefficient of the species); immunofluorescense, enzyme-linked immunosorbent assay, or similar (to test if the species interacts properly with structures on an test object known to give a positive result in the test) and; bacteriological tests (to prove that the species is sterile), can be mentioned.

Figure 2:
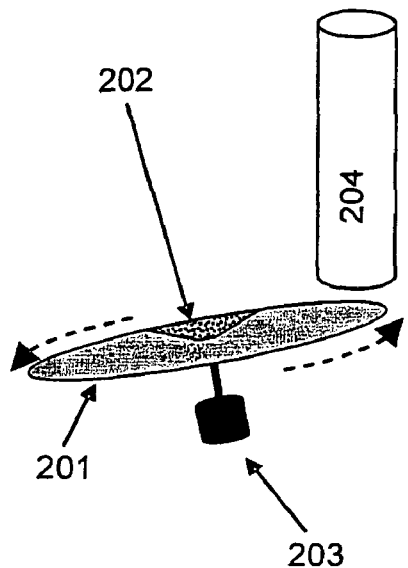
FIG. 2 shows a suitable instrument, known in prior art, for performing the measurement in the quality control method.

A preferred method for completing steps 121, 122, and 123 in FIG. 1 has been previously disclosed [WO2005080967, which is incorporated by reference herein] and is schematically described in FIG. 2. In brief, the method relies on a target (202) being immobilized to a defined area on a solid support (201), denoted an "active area". On the same solid support, there is also a reference area (in this case opposite to the active area). A liquid containing a dissolved ligand is in contact with the solid support to enable an interaction between target and ligand. Furthermore, the solid support is inclined and slowly rotated using a motor (203). Over the elevated portion of the solid support, a detector capable of detecting the label attached to the species used is mounted (204). Said detector is typically not in contact with the solid support, but registers e.g. emitted radiation of radioactive nuclides or emitted light from fluorescent labels. When the active area passes the detector, an elevated signal will be registered in case the ligand has bound to the target. The rate of ligand-target formation can be followed by depicting the difference between the detected signal from active area and reference area over time.

Many quality control measurements on reagents used in analytical or diagnostic or therapeutic procedures relies on the interaction of the reagent with a structure known to mimic the model. Such interactions may be very complex, but a general understanding of the mechanisms behind the interaction can be understood by use of simple mathematical modeling. One common description of how protein interacts is the monovalent interaction model, as discussed in detail in WO2005029077 (which is incorporated by reference herein). This interaction model is described together with an example in FIG. 3, wherein protein A (301) is interacting with protein B (302) thereby forming the complex AB (303). The quantity of complexes as well as the time required to reach equilibrium is dictated by the velocities association rate ($k_{on}$, 310) and dissociation rate ($k_{off}$, 311). Since both $k_{on}$ and $k_{off}$ are assumed to be greater than zero, there will always be free A, free B and complex AB available. It is known that the velocities $k_{on}$ and $k_{off}$ can vary considerably as discussed in the report "Label-free kinetic binding data as a decisive element in drug discovery" by Karl Andersson, Robert Karlsson, Stefan Löfås, Gary Franklin and Markku D Hämäläinen published in Expert Opinion in Drug Discovery 1(5):440-446 (which is incorporated by 4 reference herein). The impact of different $k_{on}$ and $k_{off}$ on interaction binding traces is schematically shown for curves 320, 321 and 322. Assume that protein A is in liquid phase and proteinB is found in the model attached to the solid support. At time point 330, liquid containing a known concentration of A is put in contact with the solid support. Immediately complexes will be formed with velocity $k_{on}$. After some time, there will be a balance between $k_{on}$ and $k_{off}$ resulting in equilibrium. Curves 320 and 321 have the same equilibrium level but different $k_{on}$ and $k_{off}$, resulting in a short time (331) to equilibrium for curve 321 and a long time (332) to equilibrium for curve 320. Curve 322 represents a weaker binder resulting in fewer formed complexes at equilibrium, which is typical for poor performance in analytical or diagnostic or therapeutic procedures.

A traditional quality control assay quantifies the amount of bound material at one single point in time. In case the curves 320 and 321 shall be distinguished based on signal amplitude alone, the time point at which the reading is performed has to be moved forward in time in order to avoid misclassification due to noise and other disturbances.

Figure 3:
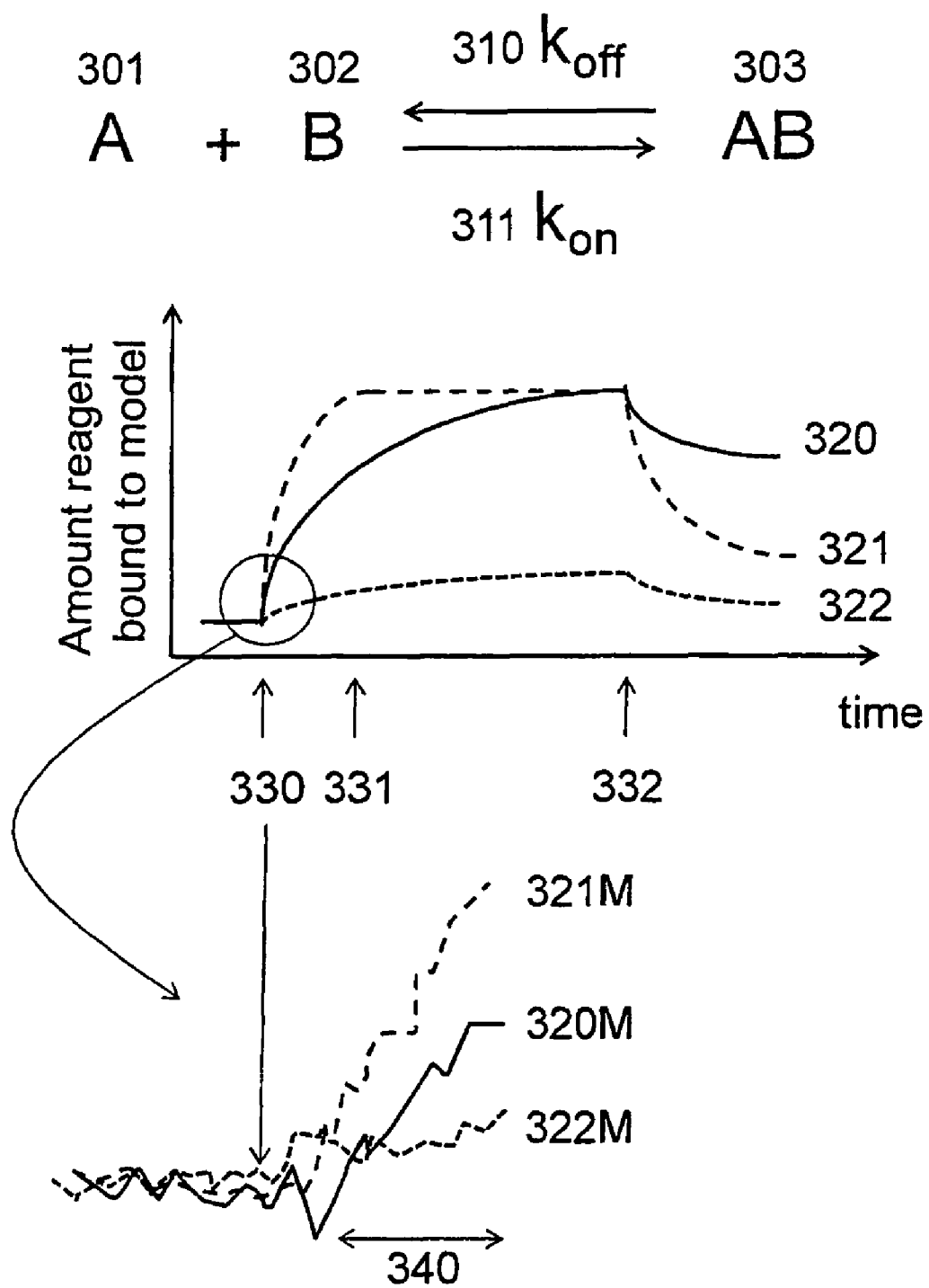
FIG. 3 shows an interaction model and schematic binding traces.

In the current invention, the read signal amplitude is complemented with a measure of the rate of complex formation. A magnified part of the curves (320M, 321M, 322M) is shown in FIG. 3. It is reasonable that the slope of the curves during time interval 340 will be a more reliable distinguishing measure than what the signal amplitude during the same time interval would. Furthermore, when adding protein A at time point 330, there is an elevated risk for signal disturbances. Such disturbances are often step-like and translate the complete curve in the y-direction, which also complicates the use of signal magnitude alone shortly after time point 330. Thus, the slope of the three curves during time interval 340 will be a better distinguishing measure than the average signal amplitude during the same time interval. By using slope measurements the time for a quality control can be reduced when compared to other endpoint measurements. This is valuable in cases where short lived radionuclides are analyzed.

The generic properties of the preferred detection method shown in FIG. 2 are the following:
- a target is immobilized to a selected portion of a solid support,
- the target is exposed to a solution containing a ligand,
- a measurement is performed, capable of detecting an interaction between said first and said second species, during which the amount of solution covering the selected portion of the support is reduced, and
- a reference measurement is performed on a portion of said support where no interaction takes place.

The predefined range used for determination of the quality of the species may be obtained is a variety of ways. One way is to test species that has been successfully used in an analytical or diagnostic or therapeutic procedure and define the obtained values as the lowest acceptable rate of complex formation and magnitude of formed complex for the particular species.

Because of the sometimes fragile nature of the species, it is of outermost importance that step 120 (FIG. 1) is performed rapidly and with limited operator intervention. The preferred method for measurement of both the rate of complex formation and the magnitude of the number of formed complexes can be completed within 15 minutes and requires only a few minutes of operator intervention. It is therefore possible to perform quality control of species at the end user site without significant delay of the analytical or diagnostic or therapeutic procedures.

It is also possible to implement the invention in reverse, i.e. by having a known species and a target of unknown quality. By immobilizing the target to a solid support, contacting the target with species, and detecting the presence of species-target interaction as well as the rate of formation of species-target interaction, an indication of the properties of target is obtained.

The following non-limiting example of the invention will illustrate the principle behind it.

EXAMPLE

The method described above was tested with a model comprising a human cancer cell-line, A431 cells, grown on one quarter of a 10 cm circular cell-dish. A431 cells are known to have high levels of EGF receptors on their surface. The antibody cetuximab was selected as species, because cetuximab has been used for targeted radiotherapy in animal trials (described in the report "(89) Zr as a PET surrogate radioisotope for scouting biodistribution of the therapeutic radiometals (90)Y and (177)Lu in tumor-bearing nude mice after coupling to the internalizing antibody cetuximab." by Perk L R, Visser G W, Vosjan M J, Stigter-van Walsum M, Tijink B M, Leemans C R, van Dongen G A published in Journal of Nuclear Medicine 2005 November; 46 (11) 1898-906, which is incorporated by reference herein). Furthermore, cetuximab is known to bind to the EGF receptor. The dish was placed in a device previously disclosed in WO2005080967 [which is incorporated by reference herein] wherein the dish was rotated with a speed of approximately 6 rounds per minute. 2 ml of liquid containing cetuximab labeled with $^{125}$I was added to the cell-dish. Since cetuximab is known to bind to the cells, the measured radioactivity will be higher when the area of the cell-dish holding target cells passes by the detector compared to other times. This gives a continuous wave-like time series of measured radioactivity where the period is determined by the angular speed of the dish and the amplitude by the amount of cetuximab binding to the cells. Initially, the amplitude of the wave-like pattern will increase as a result of continuous binding of cetuximab to the EGF receptors. In FIGS. 4(*a*) and 4(*b*), the amplitude of the wave-like pattern is plotted versus time for the initial 13 minutes of measurement. Results from two independent experiments are shown, one in FIG. 4(*a*) and one in FIG. 4(*b*). As seen in the plots, both measurements resulted in an increase in amplitude of approximately 30 counts per seconds during the first 13 minutes. The absolute signal levels after 13 minutes were 84 and 67 counts per seconds, respectively. The initial absolute signal level will depend largely on the number of cells present on the solid support, while as the initial increase in amplitude will depend largely on the properties of the interaction of cetuximab and EGF receptor. Since the exact number of cells present immobilized to each unique cell-dish will vary, the rate of formed complexes between cetuximab and EGF receptor is a preferable measure of proper function of cetuximab. To be on the safe side, both the absolute amplitude after e.g. 13 minutes and the increase of amplitude during the first e.g. 13 minutes should exceed predefined values in order recommend use in analytical or diagnostic or therapeutic applications. Suitable predefined values in this particular case are (i) absolute amplitude after 13 minutes greater than 60 counts per seconds and (ii) increase in amplitude during the first 13 minutes greater than 25 counts per seconds.

Although the invention has been described with regard to its preferred embodiment, which constitute the best mode currently known to the inventor, it should be understood that various changes and modifications as would be obvious to one having ordinary skill in this art may be made without departing from the scope of the invention as set forth in the claims appended hereto.

The invention claimed is:

1. A method for quality testing/control of radioactive species,
    wherein said species comprises macromolecules or chemical compounds;
    said species being either inherently radioactive or labeled with a radioactive nuclide;
    said species being used in diagnostic or therapeutic procedures, the method comprising:
    providing a model system for the diagnostic or therapeutic system in which the species is to be used, said model system interacting with said species to form species-model complexes;
    immobilizing the model system on a solid support;
    providing a solution of the species of interest;
    bringing said solution in contact with the model system immobilized on the support,
    detecting a presence of interaction between the species in solution and the model system on a solid support and rate of formation of species-model complexes by a radioactivity detector; and
    rejecting said species for use in a diagnostic or therapeutic procedure if the detected presence of interaction between the species and the model system and the rate of formation of species-model complexes have values deviating from predefined acceptable ranges.

2. The method as claimed in claim 1, wherein said detection is performed without bringing said detector in contact with said solid support.

3. The method as claimed in claim 1, wherein the step of detecting the presence of interactions between species in solution and model system on a solid support, further comprises:
    immobilizing the model system on a selected portion of the solid support;
    reducing the amount of solution covering the selected portion of the support prior to performing said detection;
    performing a reference measurement on a portion of said solid support at a location where no interaction takes place.

4. The method as claimed in claim 3, wherein a difference between detection and reference measurements is calculated.

5. The method as claimed in claim 1, wherein the method is performed at a hospital, a clinical chemistry laboratory, or a general health care provider.

6. The method as claimed in claim 1, wherein the solid support is a substantially flat dish capable of holding a solution confined within its boundaries.

7. The method as claimed in claim 3, wherein the reduction of the amount of solution is achieved by orienting the support at an angle that deviates from horizontal to provide an elevated part and a lower part of said support, such that the elevated part is covered by less solution than the lower part, and wherein the support is rotated at a predetermined speed of rotation.

8. The method as claimed in claim 3, wherein the solid support is a substantially flat dish capable of holding a solution confined within its boundaries.

9. The method as claimed in claim 4, wherein the reduction of the amount of solution covering the selected portion of the support prior to performing said detection is achieved by orienting the support at an angle that deviates from horizontal to provide an elevated part and a lower part of said support, such that the elevated part will be covered by less solution than the lower part, and wherein the support is rotated at a predetermined speed of rotation.

10. The method as claimed in claim 1, wherein said radioactive species has a half-life shorter than 8 days.

* * * * *